United States Patent
Lehman

(10) Patent No.: US 11,020,557 B1
(45) Date of Patent: Jun. 1, 2021

(54) MEDICAL FACE MASK

(71) Applicant: POM Medical, LLC, Simi Valley, CA (US)

(72) Inventor: Edward Lehman, Las Vegas, NV (US)

( * ) Notice: Subject to any disclaimer, the term of this patent is extended or adjusted under 35 U.S.C. 154(b) by 127 days.

(21) Appl. No.: 16/174,544

(22) Filed: Oct. 30, 2018

Related U.S. Application Data

(60) Provisional application No. 62/579,960, filed on Nov. 1, 2017.

(51) Int. Cl.
| | |
|---|---|
| *A61M 16/00* | (2006.01) |
| *A61M 16/06* | (2006.01) |
| *A61B 5/08* | (2006.01) |
| *A61M 16/22* | (2006.01) |
| *A61M 16/20* | (2006.01) |

(52) U.S. Cl.
CPC ............ *A61M 16/06* (2013.01); *A61B 5/082* (2013.01); *A61M 16/0616* (2014.02); *A61M 16/0683* (2013.01); *A61M 16/208* (2013.01); *A61M 16/22* (2013.01)

(58) Field of Classification Search
CPC .... A61M 16/06; A61M 16/22; A61M 16/208; A61M 16/0683; A61M 16/0616; A61M 16/0685; A61M 16/125; A61B 5/082
See application file for complete search history.

(56) References Cited

U.S. PATENT DOCUMENTS

| | | | | |
|---|---|---|---|---|
| 6,631,713 B1* | 10/2003 | Christopher | ...... | A61M 16/0488 128/200.21 |
| 8,365,734 B1* | 2/2013 | Lehman | ................ | A61M 16/12 128/206.28 |
| 8,960,195 B2* | 2/2015 | Lehman | .............. | A61M 16/125 128/206.28 |
| 2003/0024533 A1* | 2/2003 | Sniadach | .............. | A61M 16/06 128/205.25 |
| 2003/0047189 A1* | 3/2003 | Kumar | .................. | A61M 16/06 128/206.29 |
| 2013/0197303 A1* | 8/2013 | Chun | .................... | A61M 16/06 600/103 |

* cited by examiner

*Primary Examiner* — Steven O Douglas
(74) *Attorney, Agent, or Firm* — John Rizvi; John Rizvi, P.A.—The Patent Professor®

(57) ABSTRACT

A medical face mask is provided which includes a mask body having a mask interior and contoured to fit against the face of a patient. A permanently-open nasal aperture is provided in the mask body to facilitate insertion of an equipment, instrument or device into the mask interior and into the nose of the patient. A permanently-open oral aperture is provided in the mask body to facilitate insertion of an equipment, instrument or device into the mask interior and into the mouth of the patient. A one-way oxygen port is provided in the mask body to facilitate introduction of oxygen and/or medical gases into the mask interior of the mask body. A one-way valve port is provided in the mask body to facilitate discharge of carbon dioxide from the mask interior. A capnography or gas sampling port may be provided in the mask body to capture gases for analysis.

14 Claims, 10 Drawing Sheets

MEDICAL FACE MASK

CROSS-REFERENCE TO RELATED APPLICATIONS

This application claims the benefit of U.S. Provisional Patent Application Ser. No. 62/579,960, filed on Nov. 1, 2017, which is incorporated herein in its entirety.

FIELD OF THE INVENTION

The present invention relates generally to medical masks, and more particularly, to a medical face mask which may be used to administer low or high concentrations of oxygen and/or medical gases to a patient during procedures which may require insertion of an equipment, instrument or device into the nasal and/or oral passageway of the patient.

BACKGROUND OF THE INVENTION

A medical face mask is a commonly used medical device which facilitates introduction of oxygen and/or anesthetic or other medical gases to the lungs of a patient. A conventional medical face mask may be configured to engage the face and cover the nose and mouth of the patient in an airtight or non-airtight manner. Medical face masks are typically fabricated of a resilient material such as plastic, silicone or rubber and are typically disposable.

Medical face masks may be attached to the head of a patient by extending an elastic headband around the patient's head such that the recoil in the headband pulls against and maintains the mask in position on the face of the patient. Medical face masks may be transparent to enable healthcare providers to assess the patient and to reduce the patient's perception of claustrophobia.

Medical face masks may facilitate accuracy in the quantities or doses of oxygen and/or anesthetic or other medical gases which are administered to a patient in various medical applications. It must be noted that excess or insufficient quantities of oxygen or other medical gases are potentially harmful to a patient's health. Because of this, the quantities of oxygen and medical gases and oxygen/gas mixtures which are administered to a patient are normally closely monitored. Thus, the design of a medical oxygen mask is important to the proper delivery of oxygen and medical gases in the proper doses to the patient.

Accordingly, there is an established need for a medical face mask which may be used to administer low or high concentrations of oxygen and/or medical gases to a patient during procedures which may require insertion of an equipment, instrument or device into the nasal and/or oral passageway of the patient.

SUMMARY OF THE INVENTION

The present invention is directed to a medical face mask which may be used to provide low or high concentrations of oxygen and/or medical gases to a patient during procedures which may require insertion of an equipment, instrument or device into the nasal and/or oral passageway of the patient. The medical face mask may include a mask body which has a mask interior and is contoured to fit against the face of a patient. The mask body may include a nose covering portion which covers the nose and a mouth covering portion which covers the mouth of the patient. A permanently-open nasal aperture may be provided in the nose covering portion to facilitate insertion of an equipment, instrument or device through the mask interior and into the nose of the patient. A permanently-open oral aperture may be provided in the mouth covering portion to facilitate insertion of an equipment, instrument or device through the mask interior and into the mouth of the patient. A one-way oxygen port may be provided in the mask body to facilitate unidirectional introduction of oxygen and/or medical gases into the mask interior of the mask body. A one-way valve port may be provided in the mask body to facilitate unidirectional discharge of carbon dioxide and/or other gases from the mask interior. A capnography or gas sampling port may be provided in the mask body to capture $CO_2$ and/or other gases or for analysis.

Introducing an illustrative embodiment of the invention, the present invention includes a medical face mask which can be used to provide oxygen and/or medical gases to a patient during procedures which may require insertion of an equipment, instrument or device into the nasal and/or oral passageway of the patient, comprising:

a mask body having a mask interior, wherein the mask body comprises a mouth covering portion and a nose covering portion configured to fit over the mouth and at least the lower region of the nose of a patient, respectively;

a permanently-open nasal aperture in the mask body, the nasal aperture facilitating insertion of an equipment, instrument or device through the mask interior and into the nose of the patient;

a permanently-open oral aperture in the mask body, the oral aperture facilitating insertion of an equipment, instrument or device through the mask interior and into the mouth of the patient; and an oxygen port provided in the mask body, the oxygen port configured to facilitate introduction of breathable gas into the mask interior of the mask body.

In a second aspect, a nose arch can be shaped in the mask body to accommodate the nose of the patient.

In another aspect, the mask body can further include a mask flange along a peripheral edge of the mask body, the mask flange contoured to fit snugly against the face of the patient.

In another aspect, a nose arch can be shaped in the mask flange to accommodate the nose of the patient.

In another aspect, the mouth covering portion can include an oral aperture membrane in which the oral aperture is located.

In another aspect, the oral aperture membrane can include at least one flexible membrane flap delimiting the oral aperture.

In another aspect, the at least one membrane flap of the oral aperture membrane can be movable to adjust the size of the oral aperture.

In another aspect, the nose covering portion can include a nasal aperture membrane in which the nasal aperture is located.

In another aspect, the nasal aperture membrane can include at least one flexible membrane flap delimiting the nasal aperture.

In another aspect, the at least one membrane flap of the nasal aperture membrane can be movable to adjust the size of the nasal aperture.

In another aspect, the medical face mask can further include a one-way valve port provided in the mask body, the one-way valve port configured to facilitate discharge of gases from the mask interior.

In another aspect, the oxygen port can be arranged on a first side of the mask body and the one-way valve port can be arranged on a second side of the mask body opposite to the first side.

In another aspect, the medical face mask can further include a capnography or gas sampling port provided in the mask body and configured to capture CO2 and/or other gases from the mask interior for analysis.

In another aspect, the capnography or gas sampling port can be provided on a front side of the mask body.

In another aspect, the capnography or gas sampling port can be provided between the nasal aperture and the oral aperture.

In another aspect, the medical face mask can further include at least one strap attachment opening provided in the mask body to facilitate attachment of a mask attachment strap to the mask body.

These and other objects, features, and advantages of the present invention will become more readily apparent from the attached drawings and the detailed description of the preferred embodiments, which follow.

BRIEF DESCRIPTION OF THE DRAWINGS

Illustrative embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a medical face mask which can be used to provide low or high concentrations of oxygen and/or medical gases to a patient during procedures which may require insertion of an equipment, instrument or device such as, but not limited to, a scope, probe or tube, into the nasal and/or oral passageway of the patient.

Figure 3:
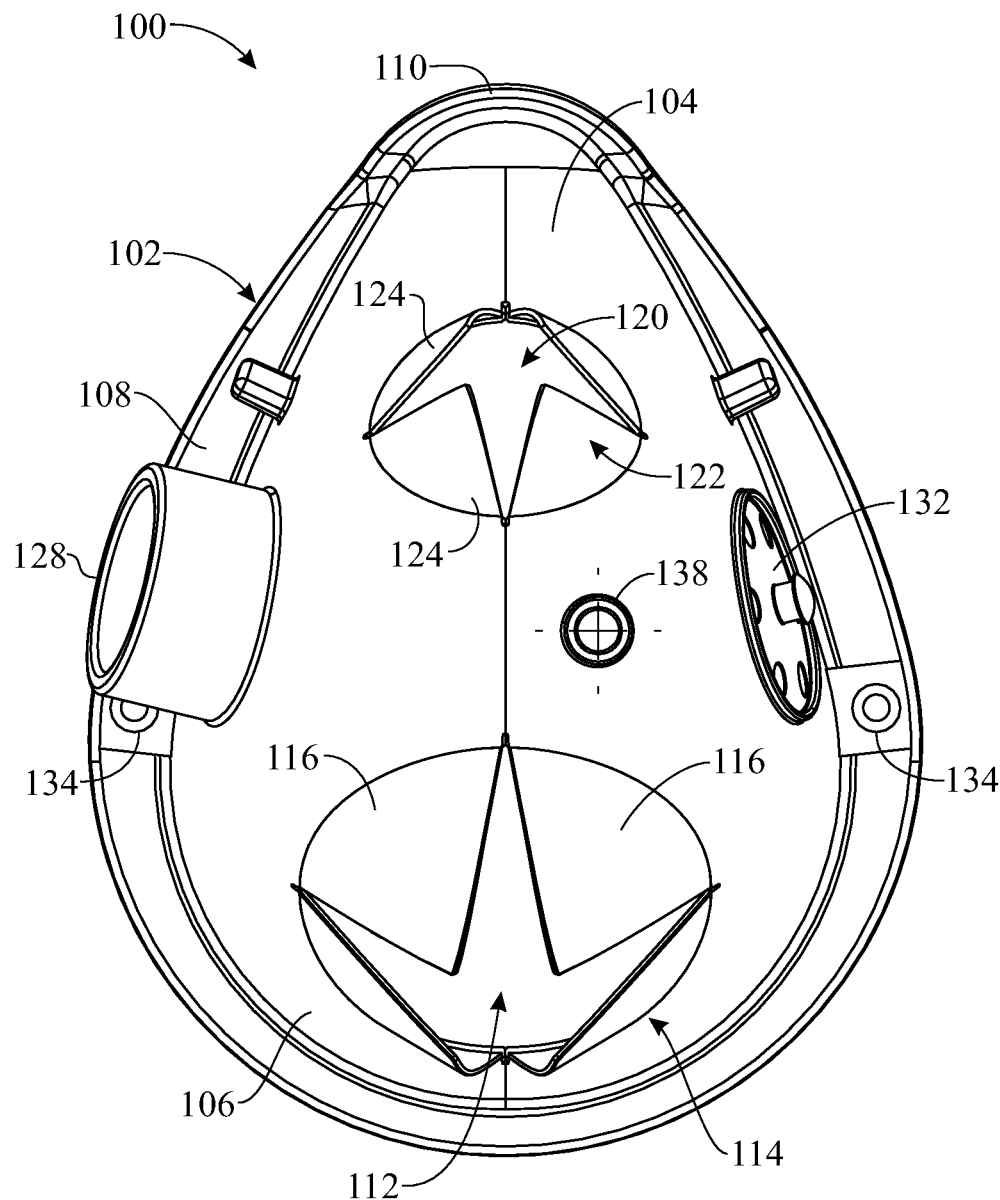
FIG. 3 presents a front elevation view of the medical face mask of FIG. 1.
Figure 4:
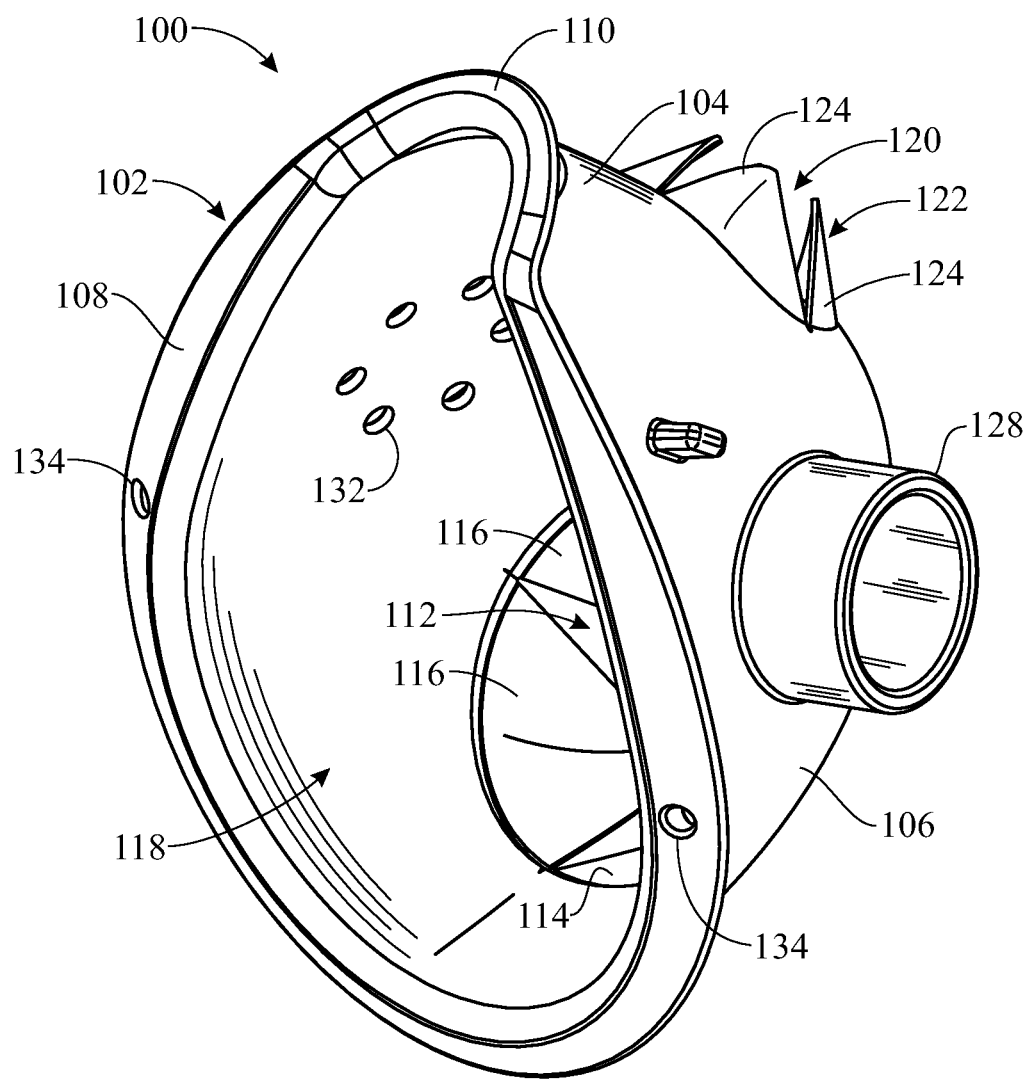
FIG. 4 presents a rear perspective view of the medical face mask of FIG. 1.
Figure 5:
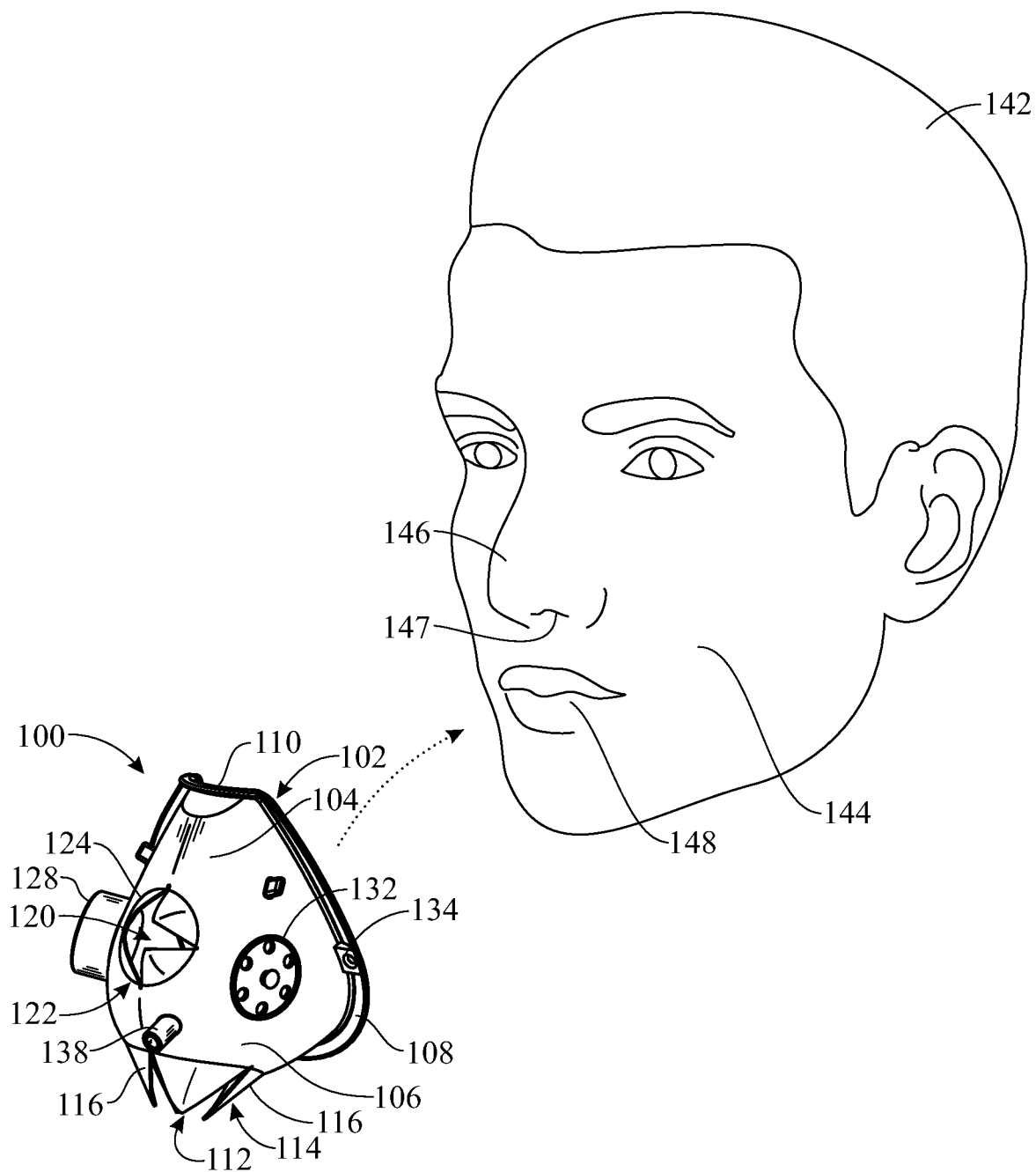
FIG. 5 presents an exploded perspective view illustrating typical placement of the medical face mask of FIG. 1 on the face of a patient.

Referring initially to FIGS. 1-4, a medical face mask 100 is illustrated in accordance with an illustrative embodiment of the present invention. As shown, the medical face mask 100 may include a mask body 102. The mask body 102 may be fabricated of plastic, silicone, rubber and/or other suitable material, and may be transparent, translucent or opaque in various implementations of the invention. The mask body 102 may be contoured to fit against the face 144 (FIG. 5) of a patient 142 in typical application of the medical face mask 100, as will be hereinafter described. The mask body 102 may include a nose covering portion 104 and a mouth covering portion 106. The nose covering portion 104 of the mask body 102 may be suitably sized and configured to at least partially cover the nose 146 (FIG. 5) of the patient 142, and more precisely, to cover at least the nostrils 147 (FIG. 5). The mouth covering portion 106 of the mask body 102 may be suitably sized and configured to cover the mouth 148 (FIG. 5) of the patient 142.

A mask flange 108 may extend around the perimeter or edge of the mask body 102. The mask flange 108 may be suitably configured to engage the face 144 of the patient 142. In some embodiments, the mask body 102 may engage the face 144 in an airtight manner; in other embodiments, the mask body 102 may instead be non-airtight. An outwardly protruding nose arch 110 may be shaped at a top of the mask flange 108 to accommodate the bridge of the nose of the patient 142. In some embodiments, a pair of strap attachment openings 134 may be provided in opposite sides of the mask body 102. The strap attachment openings 134 may facilitate attachment of a mask attachment strap, band or the like (not illustrated) to the mask body 102 for fastening of the medical face mask 100 on the head of the patient 142.

Figure 1:
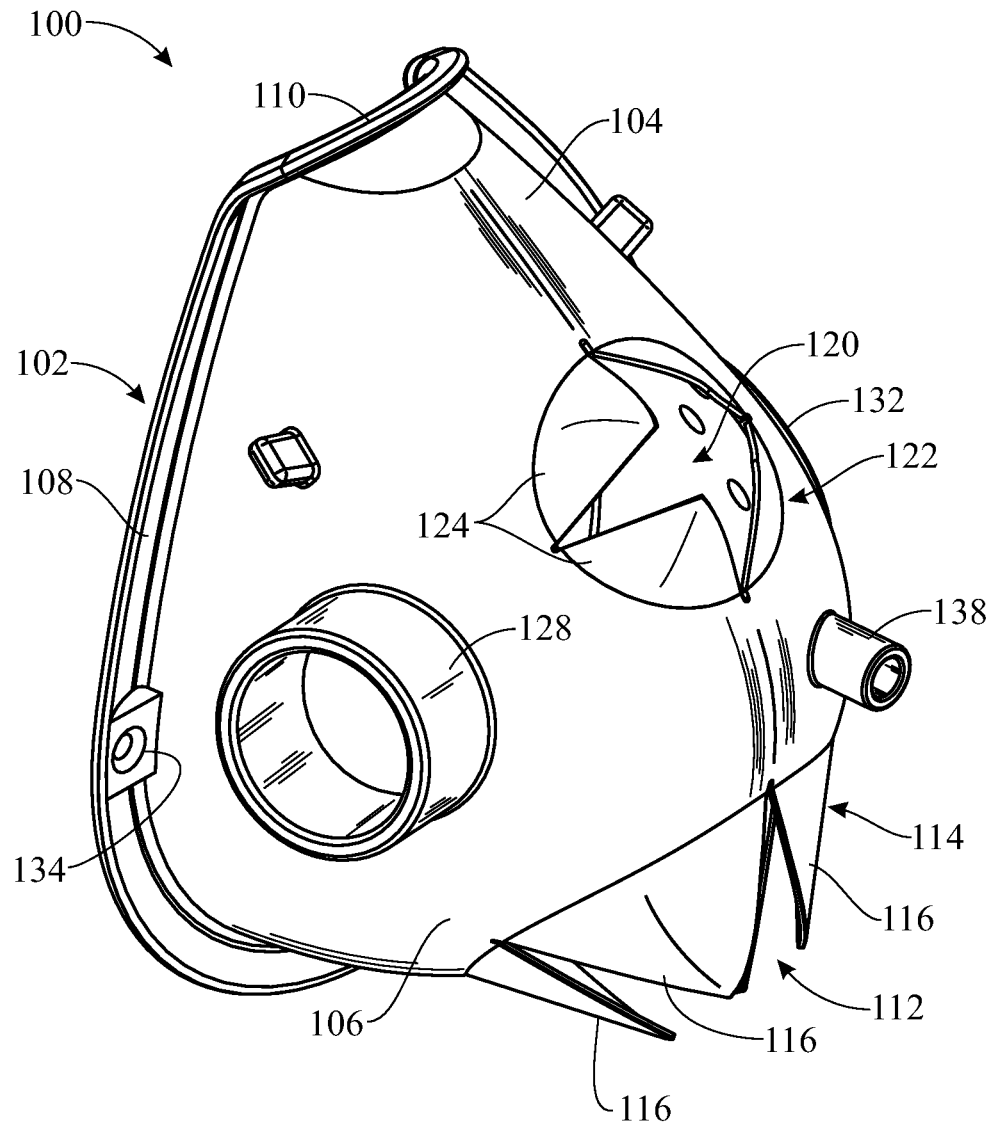
FIG. 1 presents a top front perspective view of a medical face mask in accordance with an illustrative embodiment of the present invention.

With continued reference to FIG. 1, an oral aperture 112 may be provided in the mouth covering portion 106 of the mask body 102. The oral aperture 112 may facilitate insertion of an oral scope, probe or tube 168 (FIG. 9) or other equipment, instrument or device from outside the mask body 102 into the mouth 148 of the patient 142 in typical application of the medical face mask 100, which will be hereinafter described. In the present embodiment, the oral aperture 112 is more specifically provided within an oral membrane 114 comprised in the mouth covering portion 106 of the mask body 102. In some embodiments, the oral membrane 114 may include at least one flexible membrane flap 116 which can be moved to vary the size of the oral aperture 112. For example, the at least one membrane flap 116 can be opened to increase the size of the oral aperture 112 and facilitate insertion of the oral scope, probe or tube 168 or other equipment, instrument or device through the oral aperture 112 and mask interior 118, respectively, into the mouth 148 of the patient 142.

A nasal aperture 120 may be provided in the nose covering portion 104 of the mask body 102. The nasal aperture 120 may facilitate insertion of a nasal scope, probe or tube 170 (FIG. 10) or other equipment, instrument or device from outside the mask body 102 into the nose of the patient 142 in typical application of the medical face mask 100, which will be hereinafter described. In the present embodiment, the nasal aperture 120 is more specifically provided within a nasal membrane 122 comprised in the nose covering portion 104 of the mask body 102. In some embodiments, the nasal membrane 122 may include at least one flexible membrane flap 124 which can be moved to vary the size of the nasal aperture 120. For example, the at least one membrane flap 124 can be opened to increase the size of the nasal aperture 120 and facilitate insertion of the nasal scope, probe or tube 170 or other equipment, instrument or device through the nasal aperture 120 and mask interior 118, respectively, into the nose of the patient 142.

Both the oral and nasal apertures 112 and 120 are characterized in that they are permanently open or cut within the oral and nasal membrane 114 and 122, respectively. In other words, oral and nasal membranes 114 and 122 are manufactured with the oral and nasal apertures 112 and 120 completely cut through the nasal membrane 114 and 122 in their entirety and with the membrane flaps 116 of the oral membrane 114 disengaged from one another and the membrane flaps 124 of the nasal membrane 122 also disengaged from one another, and with the membrane flaps 116 and 124 ready to be folded or moved to vary the size of the oral and nasal apertures 112 and 120 with no tearing, cracking, breaching, breaking, rupturing or splitting being required.

As further shown in FIG. 1, an oxygen port 128 may be provided in the mask body 102 to facilitate introduction of oxygen and/or medical gases into the mask interior 118 of the mask body 102. The oxygen port 128 may be a one-way valve port which permits one-way flow of gases from outside the mask body 102 into the mask interior 118. As illustrated in FIGS. 1, 3 and 4, in some embodiments, the oxygen port 128 may be provided at the side of the mouth covering portion 106 generally adjacent to the nasal aperture 120.

Figure 2:
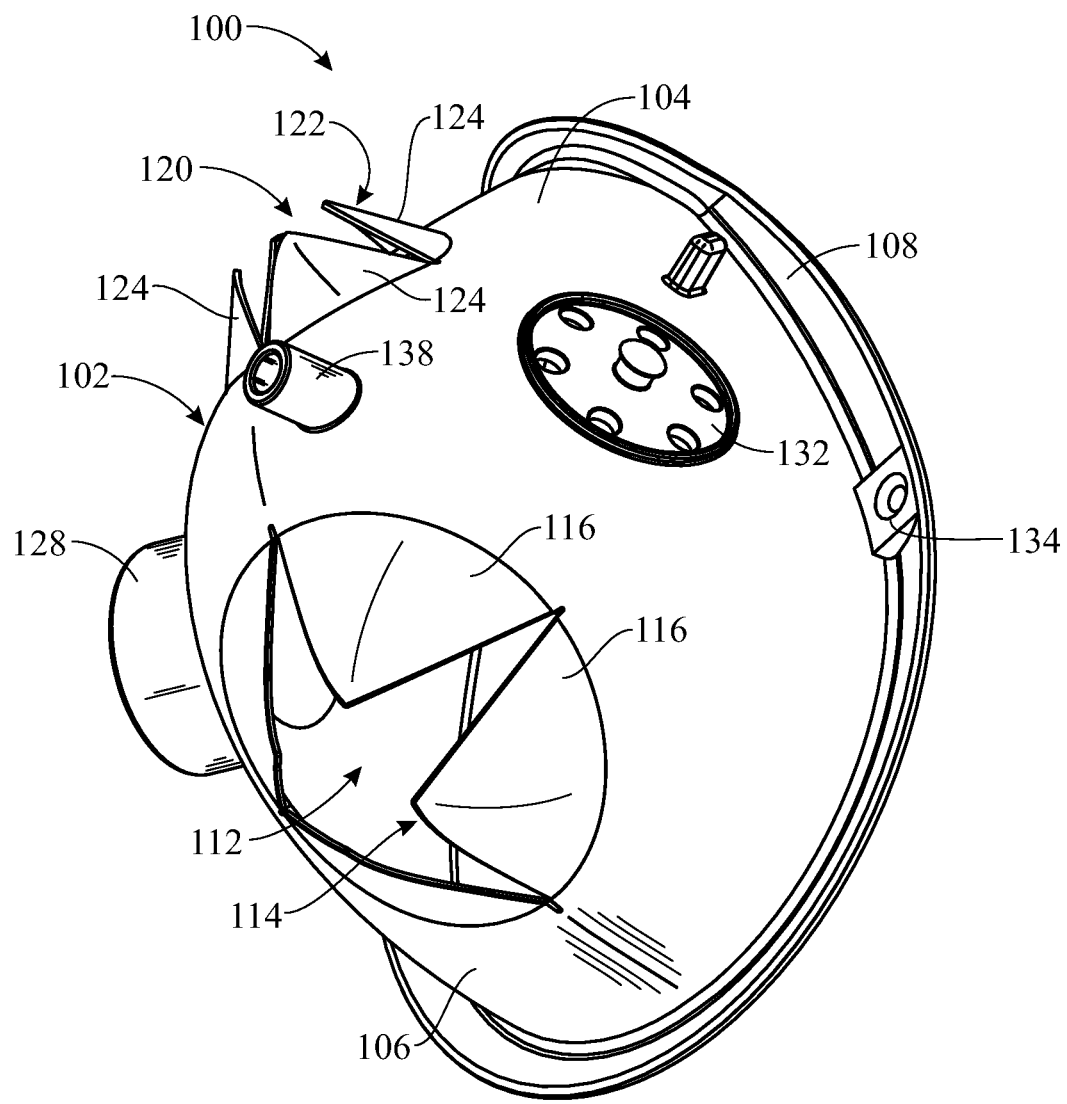
FIG. 2 presents a bottom front perspective view of the medical face mask of FIG. 1.

As illustrated in FIGS. 2 and 3, in some embodiments, a one-way valve port 132 may be provided in the mask body 102 to facilitate discharge of carbon dioxide and/or other gasses from the mask interior 118 to the exterior of the mask body 102. The one-way valve port 132 may have any design which is suitable for the purpose of facilitating discharge of gases from the mask interior 118 while preventing entry of gases into the mask interior 118. In some embodiments, the one-way valve port 132 may be provided on the side of the mouth covering portion 106 which is opposite the oxygen port 128, generally adjacent to the nasal aperture 120.

Furthermore, as shown in FIGS. 2 and 3, a capnography or gas sampling port 138 may be provided in the mask body 102 to capture respiration products of the patient 142 for analysis, as will be hereinafter described.

Figure 6:
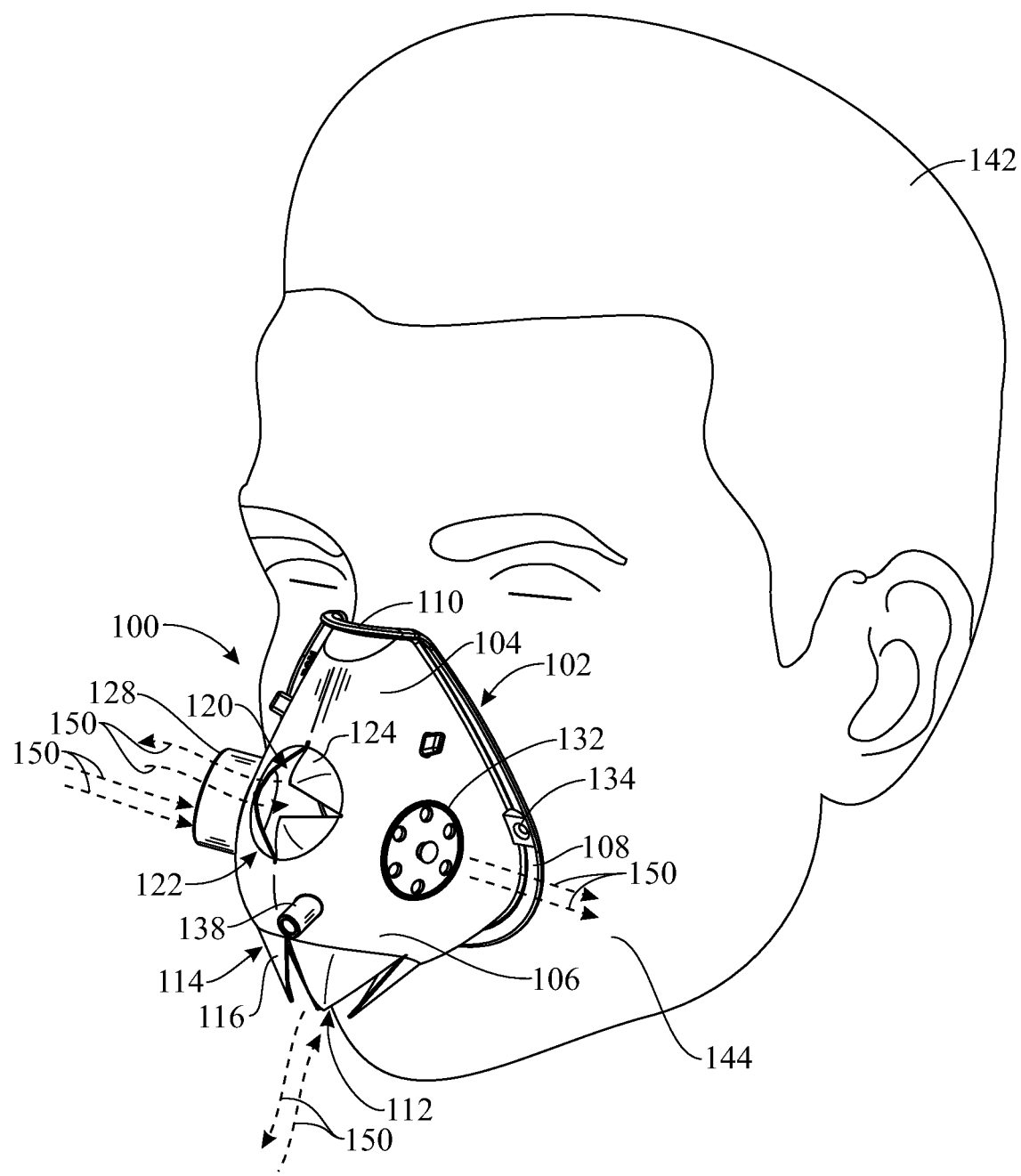
FIG. 6 presents a perspective view of the medical face mask of FIG. 1 placed on the face of the patient and being used to facilitate normal breathing of the patient.

Referring next to FIGS. 5 and 6, in typical application of the medical face mask 100, the mask flange 108 on the mask body 102 may be placed against the face 144 of the patient 142 with the nose covering portion 104 covering the nose 146 and the mouth covering portion 106 covering the mouth 148 of the patient 142. The nose arch 110 may engage the bridge of the patient's nose 146.

As illustrated in FIG. 6, as the patient 142 breathes normally, air 150 may flow bi-directionally through either or both of the oral aperture 112 and the nasal aperture 120. For this purpose, any one of the oral aperture 112 and the nasal aperture 120 may have been adjusted to a larger size by moving the corresponding membrane flaps 116 and 124 outward. Thus, the oral membrane 114 and the nasal membrane 122 may facilitate flow of air 150 into and out of the mask interior 118 and the patient's nose 146 and mouth 148. Air 150 may also flow into the mask interior 118 through the one-way oxygen port 128. Additionally, carbon dioxide may be discharged from the mask interior 118 to the exterior of the mask body 102 through the one-way valve port 132.

Figure 7:
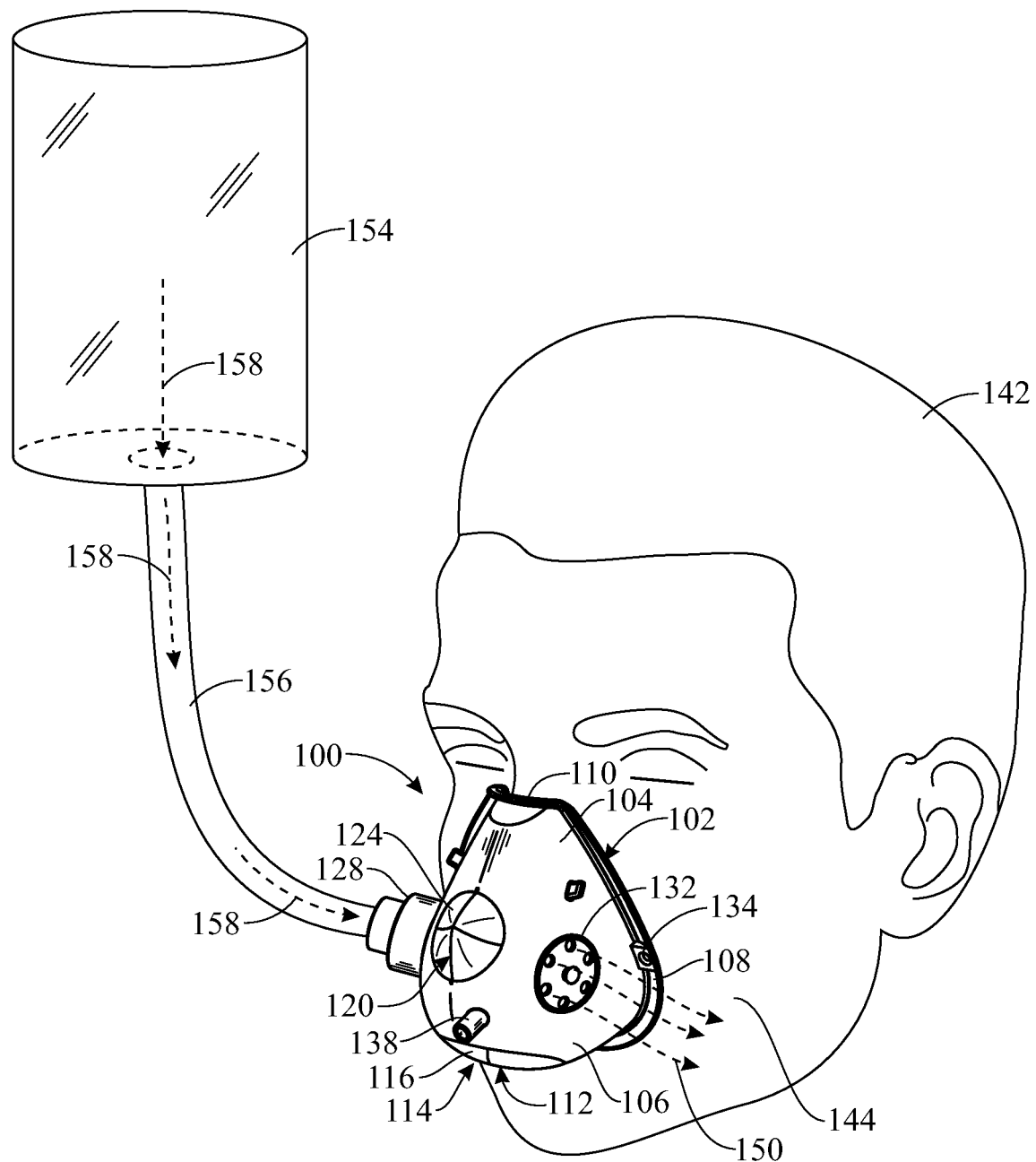
FIG. 7 presents a perspective view of the medical mask of FIG. 1 fitted on the patient's face and being used to facilitate flow of oxygen from an oxygen tank to the patient.

Referring next to FIG. 7, in some applications, an oxygen tank 154 which contains a supply of oxygen 158 may be placed in fluid communication with the one-way oxygen port 128 through an oxygen delivery tube 156. Because they may be malleable and deformable according to the pressure of gases in the mask interior 118, the membrane flaps 116 and 124 may flex into whichever position the gas pressures in the mask interior 118 demands. Alternatively or additionally, the membrane flaps 116 and 124 may have been moved inward to a more closed position (relative to the open position of FIG. 6) by manually pushing the membrane flaps 116 and 124 towards the patient's face 144. Upon subsequent termination of the flow of oxygen 158 into the mask interior 118, the reduced gas pressure in the mask interior 118 and/or manual manipulation of the membrane flaps 116 and 124 may cause the membrane flaps 116 and 124 to return to the naturally manufactured state such that the oral aperture 112 and the nasal aperture 120 are enlarged.

Figure 8:
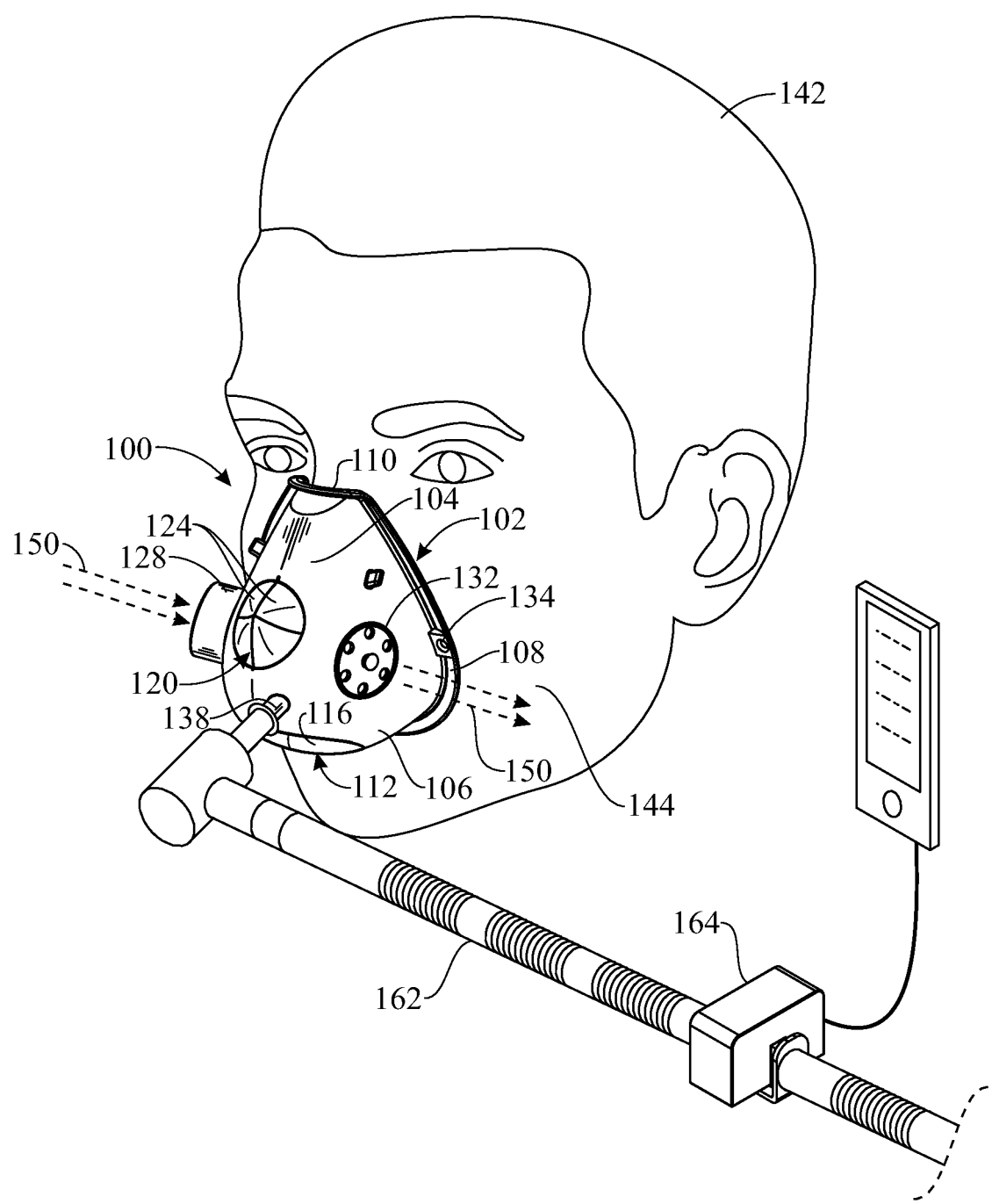
FIG. 8 presents a perspective view of the medical mask of FIG. 1 fitted on the patient's face with an illustrative capnography or gas sampling tube connected to the capnography or gas sampling port and a capnography or gas analyzer monitor connected to the capnography or gas sampling tube according to some applications of the medical face mask.

Referring next to FIG. 8, in some applications, a capnography or gas sampling tube 162 may be connected to the capnography or gas sampling port 138. A capnography or gas analyzer monitor 164 may be connected to the capnography or gas sampling tube 162. Accordingly, $CO_2$ may be expelled from the nose 146 and/or mouth 148 of the patient 142 through the capnography or gas sampling port 138 and capnography or gas sampling tube 162, respectively, to the capnography or gas analyzer monitor 164. The capnography or gas analyzer monitor 164 may analyze the captured $CO_2$ of the patient 142, such as in the conventional manner. In other applications of the invention, the capnography or gas sampling port 138 may be used to capture and monitor other respiration products or gases from the patient.

Figure 9:
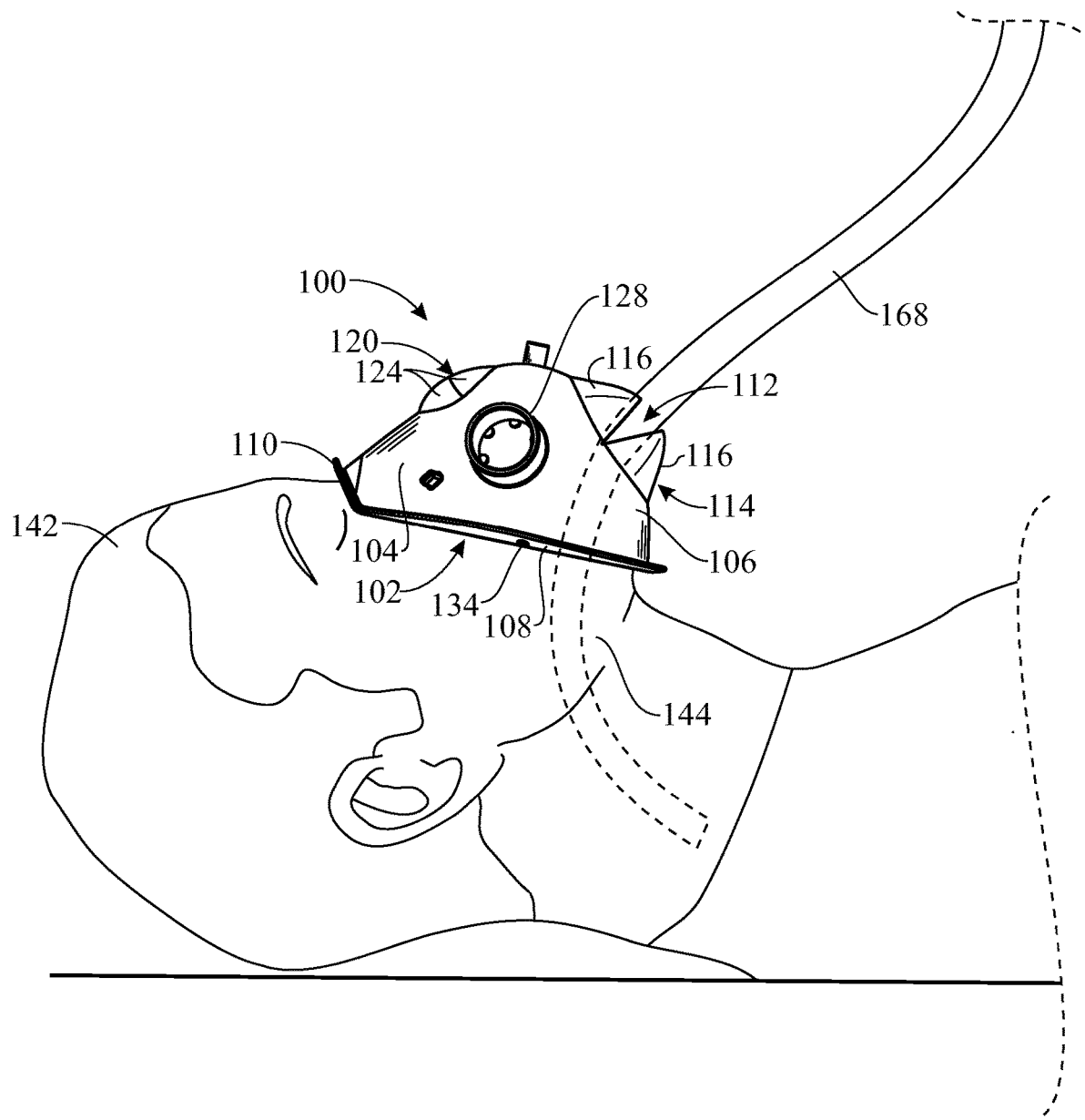
FIG. 9 presents a side elevation view of the medical face mask of FIG. 1 fitted on the face of the patient with an oral tube extending through the oral aperture into the mouth of the patient according to some applications of the medical face mask.
Figure 10:
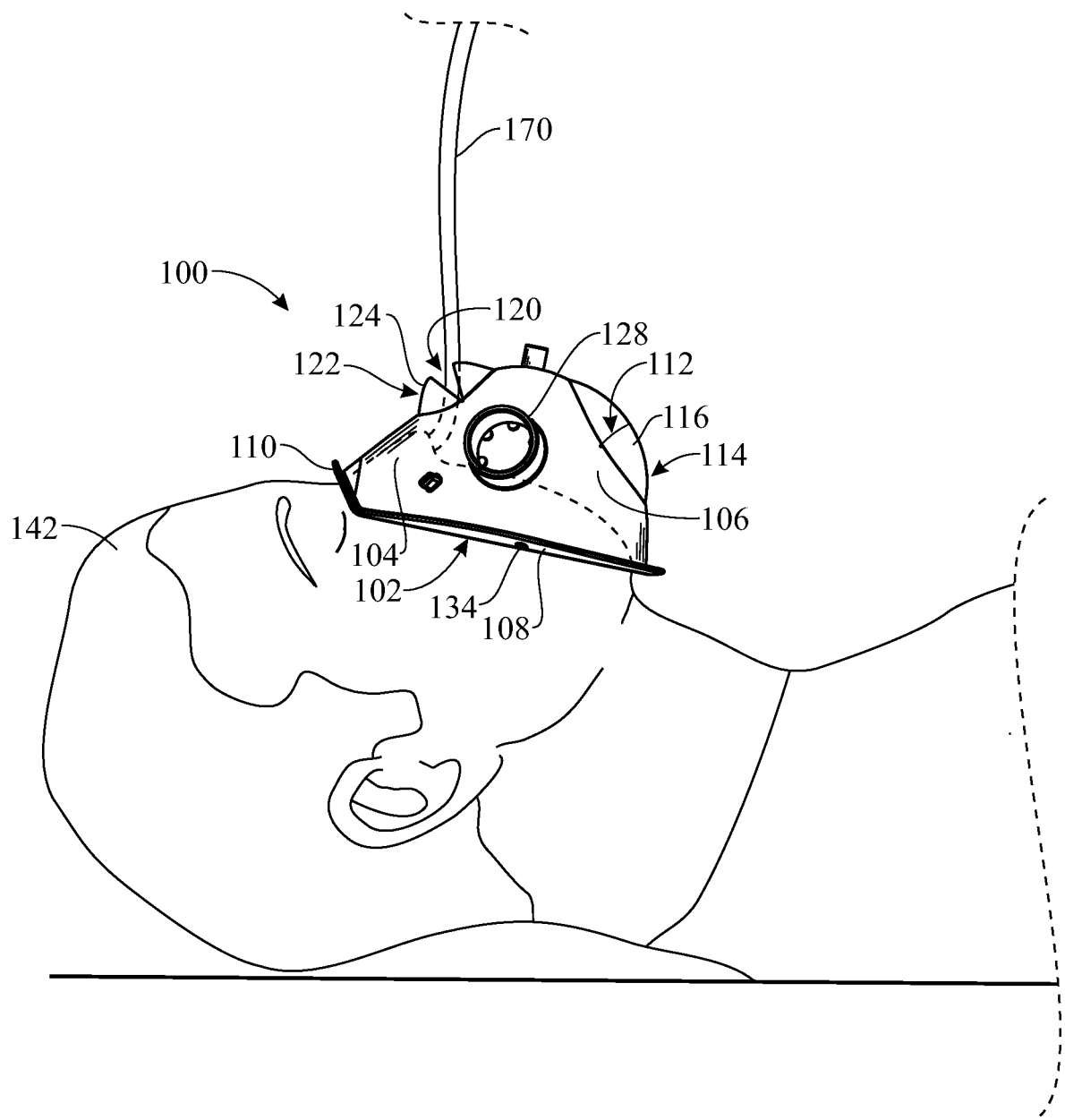
FIG. 10 presents a side elevation view of the medical face mask of FIG. 1 fitted on the face of the patient with a nasal tube extending through the nasal aperture into the nose of the patient according to some applications of the medical face mask.

Referring next to FIG. 9, in some applications, an oral scope, probe or tube 168 or other equipment, instrument or device may be inserted from outside the mask body 102 through the oral aperture 112 and mask interior 118, respectively, and into the mouth 148 of the patient 142. Alternatively or additionally, as shown in FIG. 10, a nasal scope, probe or tube 170 or other equipment, instrument or device may be inserted from outside the mask body 102 through the nasal aperture 120 and mask interior 118, respectively, and into the nose 146 of the patient 142. In some applications, oxygen 158 (FIG. 7) can simultaneously be distributed from the oxygen tank 154 through the oxygen delivery tube 156 into the oxygen port 128, as was heretofore described with respect to FIG. 7. Alternatively or additionally, the capnography or gas sampling tube 162 may be connected to the capnography or gas sampling port 138 and the capnography or gas analyzer monitor 164 connected to the capnography or gas sampling tube 162 to capture respiration products of the patient 142 for analysis, as was heretofore described with respect to FIG. 8.

Alternative embodiments are contemplated in which the medical face mask may further include one or more additional membranes to those described herein, if applicable.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A medical face mask which provides oxygen and/or medical gases to a patient during procedures which may require insertion of an equipment, instrument or device into the nasal and/or oral passageway of the patient, comprising:
    a mask body having a mask interior, wherein the mask body comprises a mouth covering portion and a nose covering portion configured to fit over the mouth and at least the lower region of the nose of a patient, respectively;
    a permanently-open nasal aperture in the mask body, the nasal aperture having at least one malleable and deformable membrane flap, wherein the at least one malleable and deformable membrane flap automatically facilitates insertion of an equipment, instrument or device through the mask interior and into the nose of the patient, and further wherein the at least one membrane flap may automatically return to an original manufactured state;
    a permanently-open oral aperture in the mask body, the oral aperture having at least one malleable and deformable membrane flap, wherein the at least one malleable and deformable membrane flap automatically facilitates insertion of an equipment, instrument or device through the mask interior and into the mouth of the patient, and further wherein the at least one malleable and deformable membrane flap may automatically return to an original manufactured state; and
    an oxygen port provided in the mask body, the oxygen port configured to facilitate introduction of breathable gas into the mask interior of the mask body.

2. The medical face mask of claim 1, wherein a nose arch is shaped in the mask body to accommodate the nose of the patient.

3. The medical face mask of claim 1, wherein the mask body further comprises a mask flange along a peripheral edge of the mask body, the mask flange contoured to fit snugly against the face of the patient.

4. The medical face mask of claim 3, wherein a nose arch is shaped in the mask flange to accommodate the nose of the patient.

5. The medical face mask of claim 1, wherein the mouth covering portion comprises an oral aperture membrane in which the oral aperture is located.

6. The medical face mask of claim 1, wherein the nose covering portion comprises a nasal aperture membrane in which the nasal aperture is located.

7. The medical face mask of claim 1, further comprising a one-way valve port provided in the mask body, the one-way valve port configured to facilitate discharge of gases from the mask interior.

8. The medical face mask of claim 7, wherein the oxygen port is arranged on a first side of the mask body and the one-way valve port is arranged on a second side of the mask body opposite to the first side.

9. The medical face mask of claim 1, further comprising a capnography or gas sampling port provided in the mask body and configured to capture $CO_2$ and/or other gases from the mask interior for analysis.

10. The medical face mask of claim 9, wherein the capnography or gas sampling port is provided on a front side of the mask body.

11. The medical face mask of claim 10, wherein the capnography or gas sampling port is provided between the nasal aperture and the oral aperture.

12. The medical face mask of claim 1, further comprising at least one strap attachment opening provided in the mask body to facilitate attachment of a mask attachment strap to the mask body.

13. A medical face mask which provides oxygen and/or medical gases to a patient during procedures which may require insertion of an equipment, instrument or device into the nasal and/or oral passageway of the patient, comprising:
    a mask body having a mask interior, wherein the mask body comprises a mouth covering portion and a nose covering portion configured to fit over the mouth and at least the lower region of the nose of a patient, respectively, wherein the mouth covering portion and nose covering portion comprise an oral aperture membrane and a nasal aperture membrane, respectively;
    a permanently-open nasal aperture in the nasal aperture membrane of the mask body, the nasal aperture having at least one malleable and deformable membrane flap, wherein the at least one malleable and deformable membrane flap automatically facilitates insertion of an equipment, instrument or device through the mask interior and into the nose of the patient and further wherein the at least one membrane flap may automatically return to an original manufactured state;
    a permanently-open oral aperture in the oral aperture membrane of the mask body, the oral aperture having at least one malleable and deformable membrane flap, wherein the at least one malleable and deformable membrane flap automatically facilitates insertion of an equipment, instrument or device through the mask interior and into the mouth of the patient and further wherein the at least one malleable and deformable membrane flap may automatically return to an original manufactured state;
    an oxygen port provided in the mask body, the oxygen port configured to facilitate introduction of breathable gas into the mask interior of the mask body; and
    a one-way valve port provided in the mask body, the one-way valve port configured to facilitate discharge of gases from the mask interior.

14. A medical face mask which provides oxygen and/or medical gases to a patient during procedures which may require insertion of an equipment, instrument or device into the nasal and/or oral passageway of the patient, comprising:
a mask body having a mask interior, wherein the mask body comprises a mouth covering portion and a nose covering portion configured to fit over the mouth and at least the lower region of the nose of a patient, respectively, wherein the mouth covering portion and nose covering portion comprise an oral aperture membrane and a nasal aperture membrane, respectively, wherein the oral aperture membrane comprises at least one malleable flexible membrane flap delimiting the oral aperture, and further wherein the at least one membrane flap of the oral aperture membrane is automatically movable to adjust the size of the oral aperture, and
the nasal aperture membrane comprises at least one malleable flexible membrane flap delimiting the nasal aperture, and further wherein the at least one membrane flap of the nasal aperture membrane is automatically movable to adjust the size of the nasal aperture;
a permanently-open nasal aperture in the nasal aperture membrane of the mask body, the nasal aperture facilitating insertion of an equipment, instrument or device through the mask interior and into the nose of the patient;
a permanently-open oral aperture in the oral aperture membrane of the mask body, the oral aperture facilitating insertion of an equipment, instrument or device through the mask interior and into the mouth of the patient;
an oxygen port provided in the mask body, the oxygen port configured to facilitate introduction of breathable gas into the mask interior of the mask body; and
a one-way valve port provided in the mask body, the one-way valve port configured to facilitate discharge of gases from the mask interior.

* * * * *